(12) United States Patent
Lee et al.

(10) Patent No.: US 6,392,064 B2
(45) Date of Patent: May 21, 2002

(54) METHOD OF SYNTHESIZING GLYCIDYL ETHER COMPOUNDS IN THE ABSENCE OF WATER AND ORGANIC SOLVENTS

(75) Inventors: Byung Min Lee; Ho-Cheol Kang; Jong-mok Park, all of Daejeon; Jung Ho Yoon, Seoul, all of (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 09/819,823

(22) Filed: Mar. 29, 2001

(30) Foreign Application Priority Data

May 1, 2000 (KR) .............................................. 00-23327

(51) Int. Cl.$^7$ ............................................. C07D 301/28
(52) U.S. Cl. ........................ 549/516; 549/514; 549/517
(58) Field of Search ................................ 549/514, 516, 549/517

(56) References Cited

U.S. PATENT DOCUMENTS 5,239,093 A    8/1993   Cheng ........................ 549/517

OTHER PUBLICATIONS

K. Urata, et al., "A Convenient Synthesis of Long–Chain 1–0–Alkyl Glyceryl Ethers", JAOCS, vol. 65, No. 8, pp. 1299–1302 (Aug. 1988).
L. Najem, et al., "Single Step Etherification of Fatty Alcohols by an Epihalohydrin", Synthetic Communications, 24(21), 3021–3030 (1994).

*Primary Examiner*—Ba K. Trinh
(74) *Attorney, Agent, or Firm*—Lowe Hauptman Gilman & Berner, LLP

(57) ABSTRACT

The present invention relates to a method of synthesizing glycidyl ether compounds without the addition of solvent. In particular, the present invention provides the improved preparation of the glycidyl ethers by using fatty alcohols with epichlorohydrin in the presence of alkali metal hydroxide and phase-transfer catalysts in the appropriate molar ratios of them without water and organic solvents.

11 Claims, No Drawings

METHOD OF SYNTHESIZING GLYCIDYL ETHER COMPOUNDS IN THE ABSENCE OF WATER AND ORGANIC SOLVENTS

BACKGROUND OF THE INVENTION

1. Field of the Invention

The present invention relates to a method of synthesizing glycidyl ether compounds without the addition of solvent. In particular, the present invention provides the improved preparation of the glycidyl ether by using fatty alcohol with epichlorohydrin in the presence of alkali metal hydroxide and phase-transfer catalyst in an appropriate molar ratio of them without water and organic solvents.

Therefore, the synthetic method of glycidyl ether compounds according to this invention has the following advantages:

First, the direct merits due to using a solid base are as follows; i) the degree of the corrosion of a reactor can be reduced owing to the non-use of aqueous basic solution, ii) an additional device for preparing an aqueous basic solution is not required since a solid form of base is directly added to the reactor containing other reactants, iii) since the by-products such as sodium hydroxide and sodium chloride can be easily separated into a solid form, they can be handled conveniently, i.e., delivery, storage and separation, and iv) additional devices for solidifying and neutralization processes of by-products are not necessary since solid by-products such as sodium hydroxide and sodium chloride are produced by this method.

Second, more amounts of reactants can be added to the reactor because of non-use of any solvent in this method. Thus, better productivity per unit size of the reactor can be ensured.

Third, the generally-available, low-priced phase-transfer catalysts are used in the reaction.

Fourth, the amounts of reactants such as alkali metal hydroxide and epichlorohydrin used in this method can be reduced in comparison with those in the conventional methods.

Fifth, this method gives much higher yield than those of the conventional methods for glycidyl ether compounds.

Therefore, the method of the present invention is suitable for the commercial mass-production.

2. Description of the Prior Art

The glycidyl ether compounds are very important intermediates in physical and phamaceutical applications such as preparing softner, antistatic agent, pseudo-ceramide, emulsifier and surface treatment agent.

There are two typical conventional methods for preparing glycidyl ether compounds. The first method is to react fatty alcohol with epichlorohydrin in the presence of Lewis acid, as shown in the following scheme 1, Scheme 1

(a)

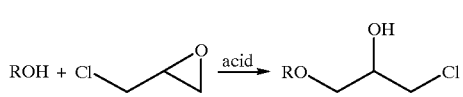

-continued (b)

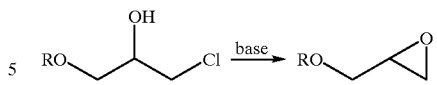

wherein R represents an alkyl group.

The reaction step (a) is performed in the presence of Lewis acid such as sulfuric acid, perchloric acid and trifluoroborane. Further, the reaction step (b) is performed with basic solution in an anhydrous organic solvent. However, the reaction of alcohol with epichlorohydrin in the presence of Lewis acid has some disadvantages, i.e., the formation of halohydrin ether and polymerization of compounds in the reaction system. Also, other reaction vessels should be required because of the two-step reactions.

For these reasons, the second conventional method, the reaction of fatty alcohol with epichlorohydrin using aqueous sodium hydroxide solution and non-polar solvent such as hexane including phase-transfer catalysts, is more useful than the reaction mentioned above for the preparation of glycidyl ether, as shown in the following scheme 2, Scheme 2

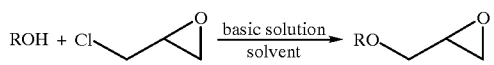

wherein R represents an alkyl group.

Recently, M. E. Borredon has reported that the yields for various glycidyl ethers through the reaction of alcohol/epichlorohydrin/base (the molar ratio of 1/2/3) in the presence of aqueous basic solution and hexane are between 39 and 76%. [*Syn. Comm.*, 24: 3021 (1994)].

Further, K. Urata has reported that through the reaction of alcohol/epichlorohydrin/base (the molar ratio of 1/2/3) in the presence of basic solution, hexane and phase-transfer catalyst, the glycidylether compound of 72–86% can be obtained [*J. Am. Oil. Chem. Soc.*, 65:1299(1988)].

The conventional one-step synthesis, Scheme 2, has faced several shortcomings in that since 3.5 fold-amount of solvent compared to the composition of base and other reactants, should be necessarily added, the reaction is performed in the two phases; water phase and organic phase. Thus the main problem lies in handling the basic solution in an appropriate manner in terms of the following disadvantages: i) the corrosion of reactor should be settled, ii) separate reactor for preparing the basic solution is necessary, iii) the by-products in a liquid form cannot be easily handled due to more inconvenient delivery and storage, iv) additional reaction process is necessary for neutralizing the basic solution and solidifying the by-products, and v) the amounts of reactants such as epichlorohydrin (more than 2 mol) and base (more than 3 mol) should be excessively employed. Thus, the conventional one-step synthesis according to the scheme 2 has been uneconomical in terms of commercial production method.

SUMMARY OF THE INVENTION

To comply with these drawbacks that the conventional invention has faced, the inventor et al. have made intensive studies and as a result, noted that the glycidyl ether compounds with a very high yield can be prepared by the reaction of alcohol, epichlorohydrin, alkali metal hydroxide and phase-transfer catalyst in an appropriate molar ratios of them without addition of solvent and aqueous basic solution, thus significantly improving several problems of the conventional method. In consequence the inventor et al. have consummated this invention.

Therefore, the manufacturing method of glycidyl ether compounds according to this invention has the following advantages:

First, the direct merits due to using a solid base are as follows; i) the degree of the corrosion of a reactor can be reduced owing to the non-use of aqueous basic solution, ii) an additional device for preparing an aqueous basic solution is not required since a solid form of base is directly added to the reactor containing other reactants, iii) since the by-products such as sodium hydroxide and sodium chloride can be easily separated into a solid form, they can be handled conveniently, i.e., delivery, storage and separation, and iv) additional devices for solidifying and neutralization processes of by-products are not necessary since solid by-products such as sodium hydroxide and sodium chloride are produced by this method.

Second, more amounts of reactants used can be added to the reactor because of non-use of any solvents in this method. Thus, better productivity per unit size of the reactor can be ensured.

Third, the generally-available, low-priced phase-transfer catalysts are used in the reaction.

Fourth, the amounts of reactants such as alkali metal hydroxide and epichlorohydrin used in this method can be reduced in comparison with those in the conventional methods.

Fifth, this method gives much higher yield than those of the conventional methods for glycidyl ether compounds.

DETAILED DESCRIPTION OF PREFERRED EMBODIMENTS

The present invention is characterized by a method of synthesizing glycidyl ether compound via the reaction with fatty alcohol, epichlorohydrin, alkali metal hydroxide and amine- or ammonium-based phase-transfer catalyst in the absence of water and organic solvents.

The present invention is described in more detail as set forth hereunder.

The conventional method requires aqueous basic solutions so as to form alkoxide in the reaction of alcohol with epichlorohydrin and it has to be performed in non-polar solvent to avoid any side-reaction of base with other reactants. For more smooth reaction, a phase-transfer catalyst is usually employed in two-phase reaction between aqueous and organic phase. However, even with the addition of a phase-transfer catalyst such as tetrabutylammonium bromide in the conventional method, a variety of drawbacks is being raised: long reaction time, low yield of 72–86%, excessive use of other reactants such as epichlorohydrin and sodium hydroxide to alcohol, especially demerits associated with the use of aqueous basic solution and low productivity due to less use of reactants compared to the size of the reactor in the presence of solvent.

In contrast, according to the manufacturing process of the present invention, the reaction can be smoothly performed in a manner such that a phase-transfer catalyst selected from amine- and ammonium-based compounds is employed in an appropriate molar ratio, together with solid alkali metal hydroxide. Based upon this, various problems associated with the use of aqueous basic solution can be avoided.

The method for manufacturing glycidyl ether compounds according to this invention is explained in more detail as set forth hereunder.

The alcohols used for this invention are a primary, secondary or tertiary alcohol compound with alkyl group containing saturated alkyl group with hydrocarbon chain or fluorocarbon chain, unsaturated alkyl group or aromatics.

The amount of epichlorohydrin, which is concurrently used with alcohol according to this invention, may vary depending upon the kinds of glycidyl ether compounds, a desired product. For example, the glycidyl ether compound, expressed by the following formula 1a, is prepared under the conditions that 0.8–4 mol of epichlorohydrin is added to 1 mol of alcohol, while 1,3-dialkyloxy-2-propanol, expressed by the following formula 1b, is prepared under the conditions that 0.12–0.7 mol of epichlorohydrin is added to 1 mol of alcohol. These molar ratios are preferred to achieve better reaction yield.

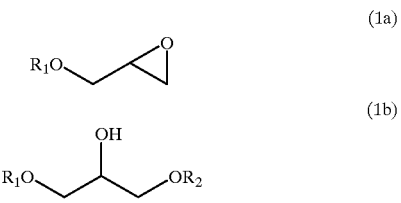

Wherein $R_1$ and $R_2$ represent independently an alkyl group containing saturated alkyl group with hydrocarbon chain or fluorocarbon chain, unsaturated alkyl group or aromatics.

According to this invention, the basic compounds used for this invention are solid alkali metal compounds, preferably alkali metal hydroxide such as sodium hydroxide and potassium hydroxide. The preferred molar ratio of base is in the range of 0.12–4 to alcohol. More specifically, the glycidyl ether compound expressed by the formula 1a is prepared in the molar ratios of 0.8–4 to alcohol, while 1,3-dialkyloxy-2-propanol expressed by the formula 1b is prepared in the molar ratios of 0.2–4 to alcohol.

Further, according to this invention, the examples of phase-transfer catalysts include amine- and ammonium-based compounds. It is preferred that the phase-transfer catalyst is employed in the molar ratios of 0.0005–0.1 to alcohol. The typical examples of the phase-transfer catalysts include trialkylamine, alkyldimethylbenzylammonium salt, tetraalkylammonium salt, N,N-dialkylamino-3-alkyloxy-2-propanol, N,N,N-trialkyl-3-alkyloxy-2-hydroxypropylammonium salt and alkyltrimethylammonium salt; hence, the anionic part of salt is selected from the group consisting of halide, methylsulfate and hydrogensulfate. The detailed examples of the phase-transfer catalysts include the following compounds, but other amine- or ammonium-based compounds may achieve the same effect, since these phase-transfer catalysts are nothing but the ones to exemplify this invention in more detail: tetrabutylammonium bromide, tetrabutylammonium hydrogensulfate, cetyltrimethylammnonium chloride,
lauryldimethylbenzylammonium chloride,
N,N-dimethylamino-3-hexyloxy-2-propanol,
N,N-dimethylamino-3-octyloxy-2-propanol,
N,N-dimethylamino-3-dodecyloxy-2-propanol,
N,N-dimethylamino-3-octadecyloxy-2-propanol,
N,N-dimethylamino-3-(1'H,1'H,2'H,2'H-perfluoro) hexyloxy-2-propanol,
N,N-dimethylamino-3-(1'H,1'H,2'H,2'H-perfluoro) octyloxy-2-propanol,
N,N-bis(2-hydroxyethyl)amino-3-hexyloxy-2-propanol,
N,N-bis(2-hydroxyethyl)amino-3-octyloxy-2-propanol,
N,N-bis(2-hydroxyethyl)amino-3-dodecyloxy-2-propanol, N,N-bis(2-hydroxyethyl)amino-3-octadecyloxy-2-propanol,
N,N-bis(2-hydroxyethyl)amino-3-(1'H,1'H,2'H,2'H-perfluoro)hexyloxy-2-propanol,
N,N-bis(2-hydroxyethyl)amino-3-(1'H,1'H,2'H,2'H-perfluoro)octyloxy-2-propanol, N,N,N-trimethyl-3-hexyloxy-2-hydroxypropylammonium methylsulfate,
N,N,N-trimethyl-3-octyloxy-2-hydroxypropylammonium methylsulfate,
N,N,N-trimethyl-3-dodecyloxy-2-hydroxypropylammonium methylsulfate,
N,N,N-trimethyl-3-octadecyloxy-2-hydroxypropylammonium methylsulfate,
N,N,N-trimethyl-3-(1'H,1'H,2'H,2'H-perfluoro)hexyloxy-2-hydroxypropylammonium methylsulfate,
N,N,N-trimethyl-3-(1'H,1'H,2'H,2'H-perfluoro)octyloxy-2-hydroxypropylammonium methylsulfate, N,N,N-trimethyl-3-octyloxy-2-hydroxypropylammonium chloride, N,N,N-trimethyl-3-octyloxy-2-hydroxypropylammonium bromide,
N,N-bis(2-hydroxyethyl)-N-methyl-3-hexyloxy-2-hydroxypropylammonium methylsulfate,
N,N-bis(2-hydroxyethyl)-N-methyl-3-octyloxy-2-hydroxypropylammonium methylsulfate,
N,N-bis(2-hydroxyethyl)-N-methyl-3-dodecyloxy-2-hydroxypropylammonium methylsulfate,
N,N-bis(2-hydroxyethyl)-N-methyl-3-octadecyloxy-2-hydroxypropylammonium methylsulfate,
N,N-bis(2-hydroxyethyl)-N-methyl-3-(1'H,1'H,2'H,2'H-perfluoro)hexyloxy-2-hydroxypropylammonium methylsulfate,
N,N-bis(2-hydroxyethyl)-N-methyl-3-(1'H,1'H,2'H,2'H-perfluoro)octyloxy-2-hydroxypropylammonium methylsulfate, and an esterified compound of octanoic acid and N,N-dimethyl-3-octyloxy-2-propanol, and an esterified compound of hexadecanoic acid and N,N-dimethyl-3-octyloxy-2-propanol.

Further, the reaction of this invention is performed under the atmospheric pressure at 10–100° C.

Further, after the reaction of this invention is completed, some by-products such as sodium chloride and sodium hydroxide present in the reaction mixtures are filtered off. Then, the un-reacted epichlorohydrin is reused through recovery process such as distillation. The desired glycidyl ether product can be isolated and purified through a simple filtration process. Other separation process for glycidyl ether is that after the reaction mixture is dissolved in appropriate solvents such as hexane, cyclohexane, heptane, toluene, diethyl ether and dialkyl ether, the desired glycidyl ether product can be separated and purified through filtration and distillation processes.

This invention herein is explained in more detail based on the following Examples without limitations thereby.

EXAMPLE

Octanol (132 g, 1 mol) was added to a round-bottomed four-neck flask equipped with an agitator, reflux condenser and thermometer at 30° C. Tetrabutylammonium bromide (16.1 g, 0.050 mol) and sodium hydroxide (61.9 g, 1.5 mol) were further added to the flask and stirred, and then, epichlorohydrin (140.1 g, 1.5 mol) was added dropwise for 10 minutes. After the mixture was stirred for 3 hours at the same temperature, by-products such as sodium chloride and sodium hydroxide were filtered off. The unreacted epichlorohydrin was reused via recovery process such as distillation. Then, glycidyl ether compound as the desired product was obtained by a simple filtration.

The following Table 1 shows the yield of octyl glycidyl ether using each base (1.5 mol) of sodium hydroxide and potassium hydroxide from the above Example.

TABLE 1

| Base | Yield |
|---|---|
| Sodium hydroxide | 90% |
| Potassium hydroxide | 90% |

The following Table 2 shows the names and yields of glycidyl ether compounds when various alcohols and their amounts from the above Example were employed.

TABLE 2

| Alcohols | | Desired product | |
|---|---|---|---|
| Kinds | Amount (Molar ratio[a]/ molar ratio[b]) | Name of product | Yield |
| Octanol | 1.5/1.5 | Octyl glycidyl ether | 90% |
| | 0.47/1.1 | 1,3-dioctyloxy-2-propanol | 90% |
| Mixed fatty alcohol[1] | 1.5/1.5 | Alkyl glycidyl ether (alkyl = octyl or decyl) | 90% |
| | 0.47/1.1 | 1,3-dialkyloxy-2-propanol (alkyl = octyl or decyl) | 90% |
| 1H,1H,2H,2H-perfluorohexyl-1-ol | 1.5/1.5 | Alkyl glycidyl ether (alkyl = 1'H,1'H,2'H,2'H-perfluoro-hexyl) | 90% |
| | 0.47/1.1 | 1,3-dialkyloxy-2-propanol (alkyl = 1'H,1'H, 2'H,2'H-perfluoro hexyl) | 90% |
| Mixed perfluoro-alcohol[2] | 1.5/1.5 | Alkyl glycidyl ether (alkyl = 1'H,1'H,2'H,2'H-perfluoro-hexyl) or (alkyl = 1'H,1'H,2'H,2'H-perfluoro-octyl) | 90% |
| | 0.47/1.1 | 1,3-dialkyloxy-2-propanol (alkyl = 1'H,1'H,2'H,2'H-perfluoro-hexyl) or (alkyl = 1'H,1'H,2'H,2'H-perfluoro-octyl) | 90% |
| 2-Ethyl-1-hexanol | 1.5/1.5 | Alkyl glycidyl ether (Alkyl = 2'-ethyl-1'-hexyl) | 90% |
| Oleyl alcohol | 1.5/1.5 | Alkyl glycidyl ether (Alkyl = oleyl) | 90% |
| 2-Octanol | 1.5/1.5 | Alkyl glycidyl ether (Alkyl = 2'-octyl) | 90% |
| Nonylphenol | 1.5/1.5 | Alkyl glycidyl ether (Alkyl = nonylphenyl) | 90% |

[a]The molar ratio of epichlorohydrin to alcohol used.
[b]The molar ratio of sodium hydroxide to alcohol used.
[1]Mixed fatty alcohol: The mixed alcohol containing 45% of octanol and 55% of decanol.
[2]Mixed perfluoroalcohol: The mixed perfluoroalcohol containing 42% of 1H,1H,2H,2H-perfluorohexan-1-ol and 58% of 1H,1H,2H,2H-perfluorooctan-1-ol From the Example, the reactions were performed using 0.05 mol of a phase-transfer catalyst selected from amine- and ammonium-based compounds and their results were shown in the following Tables 3a and 3b.

TABLE 3a

| Phase-transfer catalyst | Yield of glycidyl ether (%) |
|---|---|
| Tetrabutylammonium bromide | 90% |
| Tetrabutylammonium hydrogensulfate | 90% |
| Cetyltrimethylammonium chloride | 90% |
| Lauryldimethylbenzylammonium chloride | 90% |

TABLE 3a-continued

| Phase-transfer catalyst | Yield of glycidyl ether (%) |
|---|---|
| N,N-dimethylamino-3-hexyloxy-2-propanol | 90% |
| N,N-dimethylamino-3-octyloxy-2-propanol | 90% |
| N,N-dimethylamino-3-dodecyloxy-2-propanol | 90% |
| N,N-dimethylamino-3-octadecyloxy-2-propanol | 90% |
| N,N-dimethylamino-3-(1'H,1'H,2'H,2'H-perfluoro)hexyloxy-2-propanol | 90% |
| N,N-dimethylamino-3-(1'H,1'H,2'H,2'H-perfluoro)octyloxy-2-propanol | 90% |
| N,N-bis(2-hydroxyethyl)amino-3-hexyloxy-2-propanol | 90% |
| N,N-bis(2-hydroxyethyl)amino-3-octyloxy-2-propanol | 90% |
| N,N-bis(2-hydroxyethyl)amino-3-dodecyloxy-2-propanol | 90% |
| N,N-bis(2-hydroxyethyl)amino-3-octadecyloxy-2-propanol | 90% |
| N,N-bis(2-hydroxyethyl)amino-3-(1'H,1'H,2'H,2'H-perfluoro)-hexyloxy-2-propanol | 90% |
| N,N-bis(2-hydroxyethyl)amino-3-(1'H,1'H,2'H,2'H-perfluoro)-octyloxy-2-propanol | 90% |
| N,N,N-trimethyl-3-hexyloxy-2-hydroxypropylammonium methylsulfate | 90% |
| N,N,N-trimethyl-3-octyloxy-2-hydroxypropylammonium methylsulfate | 90% |
| N,N,N-trimethyl-3-octyloxy-2-hydroxypropylammonium chloride | 90% |
| N,N,N-trimethyl-3-octyloxy-2-hydroxypropylammonium bromide | 90% |
| N,N,N-trimethyl-3-dodecyloxy-2-hydroxypropylammonium methylsulfate | 90% |
| N,N,N-trimethyl-3-octadecyloxy-2-hydroxypropylammonium methylsulfate | 90% |
| N,N,N-trimethyl-3-(1'H,1'H,2'H,2'H-perfluoro)hexyloxy-2-hydroxypropylammonium methylsulfate | 90% |
| N,N,N-trimethyl-3-(1'H,1'H,2'H,2'H-perfluoro)octyloxy-2-hydroxypropylammonium methylsulfate | 90% |
| N,N-bis(2-hydroxyethyl)-N-methyl-3-hexyloxy-2-hydroxypropylammonium methylsulfate | 90% |
| N,N-bis(2-hydroxyethyl)-N-methyl-3-octyloxy-2-hydroxypropylammonium methylsulfate | 90% |
| N,N-bis(2-hydroxyethyl)-N-methyl-3-dodecyloxy-2-hydroxypropylammonium methylsulfate | 90% |
| N,N-bis(2-hydroxyethyl)-N-methyl-3-octadecyloxy-2-hydroxy-propylammonium methylsulfate | 90% |
| N,N-bis(2-hydroxyethyl)-N-methyl-3-(1'H,1'H,2'H,2'H-perfluoro)hexyloxy-2-hydroxypropylammonium methylsulfate | 90% |
| N,N-bis(2-hydroxyethyl)-N-methyl-3-(1'H,1'H,2'H,2'H-perfluoro)octyloxy-2-hydroxypropylammonium methylsulfate | 90% |
| An esterified compound of N,N-dimethyl-3-octyloxy-2-propanol and octanoic acid | 90% |
| An esterified compound of N,N-dimethyl-3-octyloxy-2-propanol and hexadecanoic acid | 90% |

As described above, this invention is to provide a method for the synthesis of glycidyl ether compound smoothly in the absence of water and organic solvents and to apply effectively to the industrial production of glycidyl ether compounds in a very high productivity.

What is claimed is:

1. A method of synthesizing glycidyl ether compounds via the reaction of alcohol with epichlorohydrin in the absence of water and organic solvents, wherein said the reaction between alcohol and epichlorohydrin is conducted in the presence of alkali metal hydroxide and phase-transfer catalyst selected from amine- and ammonium-based compounds with no addition of solvent.

2. The method of synthesizing glycidyl ether compounds in the absence of water and organic solvents according to claim 1, wherein said glycidyl ether compound is alkyl glycidyl ether expressed by the following formula 1a and 1,3-dialkyloxy-2-propanol expressed by the following formula 1b,

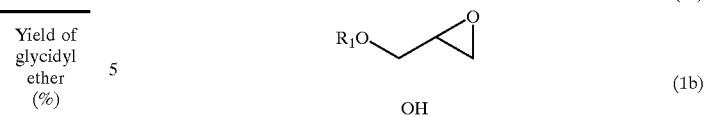

wherein $R_1$ and $R_2$ represent independently an alkyl group containing saturated alkyl group with hydrocarbon chain or fluorocarbon chain, unsaturated alkyl group or aromatics.

3. The method of synthesizing glycidyl ether compounds in the absence of water and organic solvents according to claim 1, wherein said alcohol is a primary, secondary or tertiary alcohol compound containing alkyl group containing saturated alkyl group with hydrocarbon chain or fluorocarbon chain, unsaturated alkyl group or aromatics.

4. The method of synthesizing glycidyl ethers compounds in the absence of water and organic solvents according to claim 2, wherein said glycidyl ether compound expressed by the formula 1a is prepared under the conditions where the amounts of alcohol/epichlorohydrin/base are in the molar ratios of 1/0.8–4/0.8–4.

5. The method of synthesizing glycidyl ether compounds in the absence of water and organic solvents according to claim 2, wherein said glycidyl ether compound expressed by the formula 1b is prepared under the conditions where the amounts of alcohol/epichlorohydrin/base are in the molar ratios of 1/0.12–0.7/0.2–4.

6. The method of synthesizing glycidyl ether compounds in the absence of water and organic solvents according to claim 1, wherein said phase-transfer catalyst is employed in the molar ratios of 0.0005–0.1 to alcohol.

7. The method of synthesizing glycidyl ether compounds in the absence of water and organic solvents according to claim 1 wherein said phase-transfer catalyst is selected from amine- and ammonium-based compounds.

8. The method of synthesizing glycidyl ether compounds in the absence of water and organic solvents according to claim 7, wherein said phase-transfer catalyst is selected from the group consisting of the following compounds: (a) amine-based compounds such as trialkylamine and N,N-dialkylamino-3-alkyloxy-2-propanol, or (b) ammonium-based compounds such as tetraalkylammonium salt, N,N,N-trialkyl-3-alkyloxy-2-hydroxypropylammonium salt, alkyldimethylbenzylammonium salt and alkyltrimethylbenzylammonium salt; hence, the anionic part of salt is selected from halide, methylsulfate and hydrogensulfate.

9. The method of synthesizing glycidyl ether compounds in the absence of water and organic solvents according to claim 1, wherein said reaction of alcohol with epichlorohydrin is performed under the atmospheric pressure at 10–100° C.

10. The method of synthesizing glycidyl ether compounds in the absence of water and organic solvents according to claim 1, wherein a mixture, so formed from the reaction of alcohol with epichlorohydrin, is filtered, separated and purified to obtain the desired compound directly; or said mixture dissolved in a solvent is filtered, separated and purified to obtain the desired compound.

11. The method of synthesizing glycidyl ether compounds in the absence of water and organic solvents according to claim 5 wherein said phase-transfer catalyst is selected from amine- and ammonium-based compounds.

* * * * *